United States Patent [19]

Inwood et al.

[11] Patent Number: 4,459,426

[45] Date of Patent: Jul. 10, 1984

[54] LIQUID-PHASE ALKYLATION AND TRANSALKYLATION PROCESS

[75] Inventors: Texas V. Inwood, LaHabra; Carlyle G. Wight, Fullerton; John W. Ward, Yorba Linda, all of Calif.

[73] Assignee: Union Oil Company of California, Los Angeles, Calif.

[21] Appl. No.: 447,484

[22] Filed: Dec. 7, 1982

Related U.S. Application Data

[63] Continuation-in-part of Ser. No. 143,649, Apr. 25, 1980, abandoned.

[51] Int. Cl.³ .................................................. C07C 5/22
[52] U.S. Cl. .................................... 585/323; 585/467; 585/470; 585/475
[58] Field of Search ................ 585/323, 467, 475, 470

[56] References Cited

U.S. PATENT DOCUMENTS

| | | | |
|---|---|---|---|
| 3,751,504 | 8/1973 | Keown et al. | 585/323 |
| 3,843,739 | 10/1974 | Harper et al. | 585/323 |
| 3,929,672 | 12/1975 | Ward | 252/455 Z |

*Primary Examiner*—Curtis R. Davis
*Attorney, Agent, or Firm*—Dean Sandford; Gregory F. Wirzbicki; Cleveland R. Williams

[57] ABSTRACT

A process for alkylating aromatic hydrocarbons with $C_2$ to $C_4$ olefins and for transalkylating alkyl or poly-alkylaromatic compounds with an aromatic hydrocarbon. A major portion of the aromatic hydrocarbon is recycled to the alkylation zone while the remainder thereof and poly-alkylaromatic hydrocarbons are subjected to transalkylation in a separate transalkylation zone. Mono-alkylaromatics produced in the alkylation zone are separated from the other reaction products prior to transalkylation.

39 Claims, No Drawings

LIQUID-PHASE ALKYLATION AND TRANSALKYLATION PROCESS

RELATED APPLICATIONS

This application is a continuation-in-part of copending application, Ser. No. 143,649, filed Apr. 25, 1980 and now abandoned.

BACKGROUND OF THE INVENTION

1. Field of the Invention

This invention relates to a process for the alkylation of aromatic hydrocarbons with $C_2$ to $C_4$ olefins to produce mono-alkylaromatic compounds and a mixture of poly-alkylaromatic compounds and to the transalkylation of poly-alkylaromatic compounds to produce additional mono-alkylaromatic compounds.

2. Description of the Prior Art

Processes for the alkylation and/or transalkylation of aromatic compounds with a Friedel-Crafts type catalyst (i.e., aluminum chloride, sulfuric acid, liquid and supported phosphoric acid and the like) are known and are currently practiced commercially. The above-described catalysts, however, suffer from the disadvantage of corrosion of process apparatus and waste disposal problems. Also, the supported phosphoric acid must be kept optimally hydrated, imposing an extra control function.

In addition to the above catalysts, the use of activated clays and solid zeolite catalysts has been suggested as suitable for the alkylation and transalkylation of aromatics to form alkylated aromatic compounds. In using solid zeolite catalysts, two principal modes of operation have been described. First, the catalyst may be utilized as a powder slurried in the liquid reactants. This procedure is disadvantageous because it generally requires a batch as opposed to a continuous operation, and additionally requires expensive filtration or centrifuging units to separate the catalyst from product and unreacted compounds. A more commercially feasible technique involves the use of a fixed-bed reactor containing relatively large catalyst particles through which the reacants are continuously passed.

A process for the alkylation and transalkylation of benzene with olefinic compounds is disclosed in U.S. Pat. No. 3,819,735 to Argento et al. which relates to a liquid alkylation catalyst and process for alkylating benzene with propylene or n-butene to form cumene or secondary butylbenzene. Additionally, the reference teaches a transalkylation reaction for producing secondary butylbenzene or cumene from the corresponding dialkylbenzene. The catalyst comprises a liquid, aluminum chloride which forms a liquid complex with the reactants. The liquid complex is described as having excellent room temperature stability.

Another process for the alkylation of aromatic hydrocarbons is disclosed in U.S. Pat. No. 4,169,111 to Wight which relates to a process for the manufacture of ethylbenzene. In particular, benzene is alkylated with ethylene in the presence of a crystalline zeolite catalyst to produce ethylbenzene and polyethylbenzenes. At least a portion of the diethylbenzene fraction is recycled to the alkylation zone while the remainder thereof plus higher polyethylbenzenes are subjected to a transalkylation reaction.

U.S. Pat. No. 3,417,148 to Fishel relates to an alkylation process wherein an aromatic compound, for example, benzene, toluene, xylene, etc., is alkylated with an olefin-acting compound utilizing a catalyst consisting of a crystalline aluminosilicate chemically combined with a metal subfluoride vapor. The olefin-acting compounds include olefins, acetylenic hydrocarbons, alcohol, esters, ethers, and alkyl halides. Metal subfluorides are described as aluminum monofluoride, silicon difluoride, etc.

Another alkylation process is disclosed in U.S. Pat. No. 3,586,729 to Juguin et al. which relates to a process and catalyst for alkylating aromatic hydrocarbons and/or for producing oligomers from olefins. In particular, an olefin and an aromatic hydrocarbon are contacted under alkylation conditions with a catalyst consisting of agglomerates or microballs impregnated with phosphoric anhydrides. The microballs have a specific surface area of about 200 $M^2/g$ to about 300 $M^2/g$. The reference mentions the production of ethylbenzene, cumene, and butylbenzene by alkylation.

U.S. Pat. No. 3,205,276 to Toland discloses a process for producing secondary butylbenzene from ethylene and benzene, by reacting benzene and ethylene in the presence of a polymerization-alkylation catalyst comprising aluminum metal and the reaction product of aluminum metal with a halide.

Ethylene and an aromatic compound, for example, benzene, are heated in the presence of a halide, such as hydrogen chloride, and an excess of metallic aluminum. The major product of this reaction is secondary butyl benzene.

A process for the alkylation or transalkylation of aromatic compounds is disclosed in U.S. Pat. No. 4,070,407 to Haag et al. which relates to an alkylation or transalkylation reaction wherein aromatic hydrocarbons are contacted with an alkylating or transalkylating agent in a reaction zone using a catalyst consisting of a crystalline aluminosilicate zeolite. Suitable alkylating agents are olefins, alkyl halides and alcohols. Transalkylation agents include alkyl or poly-alkylaromatic hydrocarbons.

As can readily be determined from the above, there is an ongoing search for new and more efficient processes and catalysts for producing alkylated aromatics from olefins and aromatic compounds.

Accordingly, it is an object of the present invention to provide an improved process for alkylating and transalkylating aromatic compounds.

Another object of the present invention is to provide a process for separating mono-alkylated aromatic compounds from poly-alkylated aromatic compounds prior to transalkylation, thus reducing the amount of aromatic compound and catalyst needed to efficiently transalkylate poly-aromatic compounds.

Other objects and advantages of the invention will be apparent from the following description.

SUMMARY OF THE INVENTION

The present invention resides in a process for producing alkylated hydrocarbons by contacting a mole-excess of an aromatic hydrocarbon and a $C_2$ to $C_4$ olefin in an alkylation zone under reaction conditions including the presence of a liquid phase, with an alkylation catalyst comprising a composite of a steam-stabilized hydrogen Y aluminosilicate zeolite and a mineral oxide binder, said steam-stabilized hydrogen Y aluminosilicate zeolite containing less than 0.7 weight percent of $Na_2O$ and having a unit cell size from about 24.00 Å to about 24.64 Å.

The reaction product produced in the alkylation zone is separated into fractions comprising (1) an aromatic hydrocarbon fraction, (2) a substantially pure mono-alkylaromatic fraction, and (3) a poly-alkylaromatic hydrocarbon fraction. The mono-alkylaromatic hydrocarbon fraction is recovered and a portion of the aromatic hydrocarbon fraction is recycled to the alkylation zone.

Next, a portion of the aromatic hydrocarbon fraction and the poly-aromatic hydrocarbon fraction are transalkylated in a transalkylation zone under reaction conditions including the presence of a liquid phase, in contact with a transalkylation catalyst comprising a composite of a steam stabilized hydrogen Y aluminosilicate zeolite and a mineral oxide binder, said steam-stabilized hydrogen Y aluminosilicate zeolite containing less than 0.7 weight percent of $Na_2O$ and having a unit cell size from about 24.00 Å to about 24.64 Å, wherein the transalkylation catalyst comprises a smaller amount by weight than the alkylation catalyst.

DETAILED DESCRIPTION OF THE INVENTION

The present invention resides in a process for alkylating an aromatic hydrocarbon with an olefin compound which comprises separating the alkylation reaction product into (1) an aromatic fraction, (2) a mono-alkylaromatic fraction, and (3) a poly-alkylaromatic fraction, recycling a portion of the aromatic fraction to the alkylation zone, separating an essentially pure mono-alkylaromatic compound from the reaction product and, then, transalkylating polyalkylaromatic compounds with a portion of the aromatic hydrocarbon used in the alkylation reaction utilizing as the alkylation and transalkylation catalyst an acidic, crystalline aluminosilicate zeolite, wherein said zeolite is admixed with a mineral oxide binder.

The alkylation and transalkylation catalysts herein are hydrogen Y zeolites which belong to the broad class of aluminosilicate molecular sieves characterized by, as the fundamental unit, a tetrahedral complex consisting of a small complex, for example, a silicon ion ($Si^{+4}$) in tetrahedral coordination with four oxygen atoms. The aluminum ion ($Al^{+3}$) commonly coordinates tetrahedrally, as well as octahedrally, with oxygen in zeolite formations. This coordinating ability of the aluminum ion has a profound effect on zeolite structures and their final composition. In general, the complexity of zeolite structures occurs because of the various ways in which the tetrahedral groups may link by the common sharing of oxygen ions to form polynuclear complexes.

Substitution of aluminum for a silicon ion produces a deficiency in electrical charge that must be neutralized locally by an additional positive ion within the matrix of the zeolite structure. Aluminosilicates having different structures result from differences in the manner in which the tetrahedra may link in space in either one, two, or three dimensions, and, additionally, from the types of other ions that substitute within the zeolite matrix; for example, the alkali metals or alkaline earth metals.

The alkylation and transalkylation catalyst herein is a steam-stabilized hydrogen Y aluminosilicate zeolite which is characterized by an aluminosilicate framework consisting of a diamond-like array of truncated octahedra, B-cages, linked tetrahedrally through double 6-rings and contains 8 cavities of approximately 13 Å in diameter in each unit cell. The linkage between adjoining truncated octahedra is a double 6-ring or hexagonal prism containing 12 $(Si,Al)O_2$ tetrahedra.

The unit cells are cubic with a large cell dimension of nearly 25 Å and contain 192 $(Si,Al)O_4$ tetrahedra. The chemical composition of aluminosilicate zeolite Y is related to the synthesis method. Differences in zeolite Y are related to the zeolite cation composition and distribution, the Si/Al ratio and possibly Si-Al ordering in tetrahedra sites. The aluminum ions in the unit cell of zeolite Y vary from 76 to about 48. The framework density of zeolite Y is from 1.25 to 1.29 g/cc, expressed as the number of structural framework tetrahedral per unit volume of 1,000 Å.

The alkylation and transalkylation catalyst is preferably an acidic, crystalline aluminosilicate zeolite wherein the initial sodium Y zeolite starting material utilized therein normally has a $SiO_2/Al_2O_3$ mole ratio between about 3 and 6, and contains about 10 to 14 weight percent of sodium as $Na_2O$. The sodium Y zeolite in an initial ammonium ion exchange step is digested using conventional techniques with an aqueous solution of a suitable ammonium salt, such as a chloride, nitrate, sulfate, carbonate, acetate, etc., to replace at least 20 percent, preferably at least 50 percent but not more than about 95 percent, of the original sodium ions with ammonium ions. The sodium content should be reduced to about 0.6 to 5 percent, preferably about 1 to 4 percent by weight as $Na_2O$. At this point the unit cell size of the zeolite is greater than 24.64 Å, usually between about 24.65 and 24.75 Å.

Following the initial exchange treatment, in order to produce a zeolite having the desired properties described above, it is essential that the ammonium-sodium zeolite at this stage be calcined in the presence of steam, as opposed to calcination under anhydrous conditions. As noted above, high temperatures and a substantial partial pressure of steam are necessary in order to achieve the desired hydrothermal and ammonia stability via dealumination and unit cell shrinkage. The steam treatment additionally alters the pore size distribution of the zeolite; the initial Y zeolite has uniform pore diameters of about 8 to 10 Å, while the steamed product has a substantial portion of the pore volume in pores greater than 20 Å in diameter. It should be noted that the above zeolite is water-washed after each ion exchange to remove undesirable materials.

For effective stabilization, the calcination should be carried out while maintaining at least about 0.2 p.s.i.g. water-vapor pressure, preferably about 2 to 15 p.s.i.g., especially from about 5 to 15 p.s.i.g., for a substantial time at temperatures above 600° F. Operative steaming temperatures range between about 600° F. and 1650° F. for about 0.5 minute to about 4 hours; these temperatures are sufficient to reduce the unit cell size of the zeolite below about 24.64 Å, preferably from about 24.00 Å to about 24.64 Å. This reduction in unit cell size is a convenient indication of the degree of stabilization obtained. A preferred method of preparing the aluminosilicate catalyst herein is described in detail in U.S. Pat. No. 3,929,672, the disclosure of which is incorporated herein by reference.

The steam-calcined zeolite is next re-exchanged with an ammonium salt solution under sufficiently severe conditions to reduce the remaining zeolitic sodium content of the zeolite to less than 2 weight percent, preferably to less than about 0.7 weight percent.

Following the second exchange step, the stabilized zeolite is preferably admixed with a hydrous mineral oxide binder of a difficulty reducible metal. The term hydrous is used to designate oxides having structural surface hydroxyl groups detectable by infrared analysis. Suitable oxides include alumina, silica, magnesia, beryllia, zirconia, titania, thoria, chromia, and clays and combinations thereof, such as silica-alumina, silica-magnesia and the like. It should be noted, however, that alumina is the preferred mineral oxide binder. Normally the above-described zeolite and mineral oxide binder are admixed in a weight ratio of from about 50:50 to about 95:5, preferably from about 70:30 to about 90:10, especially from about 75:25 to about 90:10. The mineral oxide binder and zeolite may be combined using conventional methods, for example, mechanical admixture or mulling. The mineral oxide binder serves not only to strengthen the admixture, but to provide a porous matrix comprising macropores in the 300 to 1,000 Å diameter range. These macropores form a three-dimensional system of intersecting channels giving improved diffusional access to the interior of the admixture.

After admixing the mineral oxide binder with the zeolite component, the mixture is normally consolidated into a granular shape desired for the final catalyst. A particularly desirable shape is a non-cylindrical extrudate having a cross-sectional configuration embracing a plurality of arcuate lobes extending outwardly from the central portion thereof, as illustrated, for example, in FIGS. 6, 7, 8, and 10 of U.S. Pat. No. 4,028,227 to Gustafson. These configurations lend strength to the extrudates, give improved diffusional access to the particle interior, and, additionally, provide more interstitial void space in the catalyst bed, thereby reducing plugging and pressure drop. Generally, the finished catalyst has a surface area ranging from about 500 $M^2/g$ to about 800 $M^2/g$; a pore volume of from about 0.5 c/g to about 0.8 cc/g; and a compacted bulk density of from about 0.45 to about 0.75. A more detailed description of how to prepare the catalysts herein is set forth in U.S. Pat. No. 3,929,672 to Ward, the disclosure of which is incorporated herein by reference. It should be noted that other catalyst configurations may be used herein. For example, catalysts in pellet, bead, or granular configuration are suitable.

Metals from Groups IA and IIA of the Periodic Table may conveniently be substituted for the sodium in the Y zeolite above using conventional techniques and methods. Operable compounds include the Group IA and Group IIA chlorides, bromides, iodides, carbonates, bicarbonates, sulfates, sulfides, thiocyanates, peroxysulfates, acetates, benzoates, citrates, fluorides, nitrates, formates, propionates, butyrates, valerates, lactates, malonates, oxalates, palmitates, hydroxides, tartrates, and the like. It is to be noted that the only limitation of the particular Group IA and Group IIA metal salt or salts employed is that it be sufficiently soluble in the ion exchange fluid medium in which it is used to give the necessary metal ion exchange.

Representative members of Group IA metals include lithium, potassium, rubidium, cesium, and francium. It should be noted that sodium is highly undesirable and is not included with the Group IA metals herein. Desirable Group IIA metals include beryllium, magnesium, calcium, strontium, barium, and radium. Normally, the Group IA or Group IIA metal is incorporated into the catalyst from about 0.1 to about 10.0 weight percent, especially from about 0.5 to about 5.0 weight percent based on the weight of the catalyst.

In a representative alkylation process, an aromatic hydrocarbon, olefin and aluminosilicate zeolite, as herein defined, are introduced into a pressure vessel having agitation means, for example, a pressure downflow or upflow tubular reactor equipped with a central longitudinal thermowell, wherein said reactor is immersed in a heating zone provided with temperature control means. Agitation is defined herein as shaking, rocking, stirring, or percolation. Either a batch or a continuous process may be used herein. When the batch method is used, an aromatic hydrocarbon, olefin and alkylation catalyst are introduced into a reaction vessel and the temperature and pressure are adjusted to the operating reaction conditions.

In a continuous process for alkylating aromatic hydrocarbons with olefins, the above-described reactants, including aluminosilicate zeolite catalyst, are continuously fed into a pressure vessel substantially as described herein at a constant rate or, alternatively, a variable rate. Normally, the aromatic hydrocarbon and olefin are contacted at a molar ratio of from about 4:1 to about 25:1, especially from about 4:1 to about 20:1, preferably from about 4:1 to about 15:1. These molar ratios maximize catalyst cycle-life while preventing the formation of excess polyalkylated aromatics.

In accordance with this invention, the aromatic hydrocarbon herein is preferably alkylated with an olefin containing a carbon chain with from about $C_2$ to about $C_4$ carbon atoms. Suitable olefins include, for example, ethylene, propylene, n-butene, butene-1, trans-butene-2 or cis-butene-2 and mixtures thereof. Aromatic hydrocarbons which are suitable for use herein are those aromatic hydrocarbons which are alkylatable under the prescribed reaction conditions. Suitable aromatic hydrocarbons include benzene, toluene, and xylenes. The preferred aromatic hydrocarbon is benzene.

In order to maintain the reaction temperature in the preferred range thus reducing the formation of unwanted polyalkylated aromatics, it is desirable to quench the reactants to dissipate heat and supply additional olefin to react with excess or unreacted aromatic hydrocarbon at various locations within the reaction zone. This is accomplished, in a single-stage reactor, by multiple injection of olefin into the reaction zone via strategically placed inlet lines leading into said reaction zone. In a multiple reactor system, for example, where a number of reactors are connected in series, olefin is injected at strategically located points within the reaction zone of each reactor. The amount of olefin injected into either the single reactor or multiple-stage reactors may be varied at each injection point according to need. For example, the amount of olefin may be added at each injection point at a mole ratio of from about 1:100 to about 100:1 in relation to the olefin in the feedstream originally introduced into the alkylation zone. Benefits resulting from multiple olefin injection include elimination of costly cooling apparatus in the process, improved selectivity to formation of the desired alkylaromatic compound, provision for a larger heat sink and optimization of the olefin to aromatic compound molar ratio throughout the reaction zone thus resulting in increased yield of the desired mono-alkylated aromatic compound. Additionally, multiple injection of olefin improves catalyst life.

Temperatures which are suitable for use in the process herein are those temperatures which initiate a reaction beween an aromatic hydrocarbon and the particular olefin used to selectively produce the desired alkylaromatic compound. Generally, temperatures suitable for use are from about 250° F. to about 550° F., especially from about 300° F. to about 500° F. Pressures which are suitable for use herein preferably are above about 50 p.s.i.g. but should not be in excess of about 2,000 p.s.i.g. An especially desirable pressure range is from about 150 p.s.i.g. to about 700 p.s.i.g.; with a weight hourly space velocity (WHSV) of from about 1 to about 50, especially from about 2 to about 40 pounds of benzene and olefin per pound of catalyst per hour. It should be noted that the temperature and pressure combination used herein is such that the alkylation and transalkylation reactions take place in essentially the liquid-phase. In a liquid phase process for producing alkylaromatics, the catalyst is continuously washed with reactants thus preventing build-up of coke precursors on the catalyst. This results in reduced amounts of carbon forming on said catalyst in which catalyst cycle life is extended as compared to a gas-phase alkylation process in which coke formation and catalyst deactivation is a major problem. Additionally, the selectivity to mono-alkylaromatic production, especially ethylbenzene production, is higher in the catalytic liquid-phase transalkylation reaction herein as compared to catalytic gas-phase transalkylation reaction.

A minor amount of the aromatic hydrocarbon and olefin from the alkylation reaction form poly-alkylaromatic hydrocarbons in addition to the desired products, for example, ethylbenzene, isopropyl benzene (cumene) or secondary butylbenzene. These undesirable poly-alkylaromatic hydrocarbons may contain two or more alkyl groups that have from 1 to about 5 carbon atoms, for example, the di, tri and tetra alkylaromatic hydrocarbons including the ortho, meta and para isomers of xylene.

The reaction product from the alkylation zone is separated into three fractions using conventional separation techniques. The three fractions comprise (1) an aromatic fraction, (2) a mono-alkylated aromatic fraction, and (3) a poly-alkylated aromatic fraction. The fraction comprising desired mono-alkylated aromatic compounds is recovered from the reaction product using conventional techniques. A portion of the aromatic fraction is recycled to the alkylation zone and a portion of the aromatic fraction is transported to the transalkylation zone. Normally, from about 25 to about 90 weight percent, preferably from about 30 to about 85 weight percent of the aromatic fraction is recycled to the alkylation zone. Next, the poly-alkylated aromatic fraction and from about 10 to 75 weight percent, preferably from about 15 to about 70 weight percent of the aromatic fraction are transalkylated.

The steam-stabilized, hydrogen Y aluminosilicate zeolite described herein is suitable for use in both the alkylation and transalkylation reactions.

The transalkylation reaction vessel is similar to the pressure vessel used in the alkylation step of the process herein. Normally, the aromatic hydrocarbon and undesirable poly-alkylaromatic compounds are introduced into the reactor at a molar ratio of from about 1:1 to about 50:1, especially from about 4:1 to about 30:1. The transalkylation reaction is conducted at a temperature of from about 250° F. to about 550° F., preferably from about 275° F. to about 500° F., with at least some of the reactant being present in the liquid phase; at a pressure of from about 50 p.s.i.g. to about 2,000 p.s.i.g., especially from about 100 p.s.i.g. to about 700 p.s.i.g., and, at a weight hourly space velocity (WHSV) of from about 0.5 to about 50 pounds of aromatic hydrocarbon and alkyl or poly-alkylaromatic hydrocarbon compound per pound of catalyst per hour, preferably from about 1 to about 15 pounds of aromatic hydrocarbon and alkyl or poly-alkylaromatic compound per pound of catalyst per hour.

One advantage of the present invention resides in a liquid-phase alkylation and transalkylation process wherein the catalyst is continuously washed with reactants thus preventing catalyst build-up of coke precursors such as polymers on said catalysts which tend to deactivate and shorten catalyst cycle life, thus resulting in longer catalyst life in the process.

Another advantage of the present invention resides in the use of a steam-stabilized hydrogen Y aluminosilicate zeolite catalyst in the alkylation and transalkylation reaction zones. This process produces only trace amounts of xylenes which have boiling points very close to the boiling point of ethylbenzene. The process in accordance with this invention usually produces less than 0.2 weight percent, preferably less than 0.1 weight percent xylenes which are highly undesirable in this process because separation of these compounds by distillation from ethylbenzene is very difficult, requiring techniques such as crystallization, etc.

Yet another advantage of this invention resides in the requirement of substantially less catalyst and aromatic compound in the transalkylation reaction zone as compared to the alkylation reaction zone. Less catalyst and aromatic compound are required because mono-alkylaromatic compounds are removed from the transalkylation feed stream entering the transalkylation reaction zone, thus reducing the amount of catalyst and aromatic compound required to transalkylate poly-aromatic compounds to mono-aromatic compounds.

Still another advantage of this invention resides in a liquid-phase alkylation and transalkylation process which requires less contact time of the reactants with the transalkylation catalyst, resulting in higher weight hourly space velocities of the pertinent reactants (i.e., aromatic, alkylaromatic and polyaromatic compounds).

The invention will be further described with reference to the following Examples.

EXAMPLE I

Benzene is alkylated with ethylene to produce ethylbenzene by introducing into two pressure reactors connected to series, 28.43 and 56.87 grams, respectively, of catalyst comprising a 90 percent acidic, crystalline aluminosilicate zeolite containing less than 0.7 weight percent of $Na_2O$, admixed with 10 percent peptized alumina, wherein said zeolite has a unit cell size from about 24.00 Å to about 24.64 Å. The catalyst has a cloverleaf, cross-sectional configuration and is admixed with 3.3 volume parts of 6 to 8 mesh, catalytically inert quartz granules per volume of catalyst. The mixture of catalyst and quartz granules are charged to the lower 24.4 inch portion of the first reactor and to the lower 48.75 inch portion of the second reactor with a preheat section consisting of quartz granules filling 48.75 inches and 24.4 inches above the catalyst-quartz mixture in each reactor. It should be noted that the upper quartz sections of the alkylation reactors serve as feed distribution and preheat areas.

The two alkylation reactors are downflow tubular reactors having a length of 123 inches, an inside diameter of 0.96 inches, and, in addition, are equipped with a 0.25 inch outside diameter, central-longitudinal thermowell. The reactors are immersed in molten-heated salt baths provided with temperature control and agitation means.

Benzene and ethylene are introduced into the first alkylation reactor through a side-arm tube located above the top of the preheat section and just above the salt bath. The effluent from the first reactor and additional ethylene is introduced into the second reactor in accordance with the method used to introduce the feed stream to the first reactor. The reaction conditions are summarized in Table 1 below.

TABLE 1

|  | 1st Alkylation Reactor | 2nd Alkylation Reactor |
|---|---|---|
| Benzene/Ethylene Mole Ratio | 8.2:1 | 10.3:1 |
| Pressure, p.s.i.g. | 500 | 500 |
| Temperature, °F. | 450 | 450 |
| Ethylene rate ratio | 1.0 | 0.7 |
| WHSV | 32.3 | 16.1 |
| Ethylene Selectivity (Based on Ethyl Groups) |  |  |
| Ethylbenzene |  | 97.00 |
| Di-ethylbenzene |  | 0 |
| Tri-ethylbenzene |  | 0.03 |
| Unknowns |  | 2.97 |

A series of three continuous, water-cooled distillation columns are used to separate the combined reactor effluents from the alkylation reactors. A portion of the overhead from the first distillation column (79.0 weight percent) is returned to the alkylation reactors as recycle benzene. The remaining overhead benzene is transported to the transalkylation reactor as recycle benzene.

The overhead from the second distillation column is ethylbenzene product which is separated from the reaction product and sent to storage facilities, and the overhead from the third distillation column is mostly poly-alkylaromatic compounds and is recycled to a transalkylation reactor together with the remainder of benzene (21.0 weight percent) from the first distillation column. Heavy reject resid from the third distillation column is discarded.

Examples of poly-alkylaromatic hydrocarbons include di-ethylbenzene, tri-ethylbenzene, and unknowns. Benzene and poly-alkylaromatic hydrocarbons substantially as described above are introduced into a transalkylation reactor similar to the first alkylation reactor with the following exception: 42.65 grams of catalyst admixed with 1.94 volume parts of 6 to 8 mesh inert quartz granules per volume of catalyst are used in the transalkylation reactor. The catalyst used in the transalkylation reactor is the same as the catalyst utilized in the alkylation reactor. The reaction conditions are summarized in Table 2 below:

TABLE 2

| Benzene/alkyl or poly-alkylaromatic mole ratio | 10:1 |
|---|---|
| Pressure, p.s.i.g. | 500 |
| Temperature | 500° F. |
| WHSV | 6.6 |

The alkylation and transalkylation reactions give the following yield as a weight percent of fresh charge materials (i.e., feed to alkylation reactors).

TABLE 3

| Product | Yield, Wt. % of Reactor Charge |
|---|---|
| Ethylbenzene | 97.0 |
| Light Ends | 1.0 |
| Resids (Heavies) | 2.0 |

It should be noted that the ethylbenzene purity is 99.80 percent.

Analysis of the reaction products in the alkylation and transalkylation reactions is conducted using a Model 3920B Perkin-Elmer gas chromatograph equipped with a flame ionization detector and a 50-foot stainless steel column having an inside diameter of 0.02 inch. The column is a SCOT OS-138, which is packed with a mixture of diatomaceous earth and polyphenyl ether. The above column is marketed commercially by the Perkin-Elmer Corporation. After liquid sample induction, the gas chromatograph is held at 60° C. for 2 minutes and thereafter programmed to increase 8° C. per minute to 190° C.

EXAMPLE II

Benzene is alkylated with propylene to produce cumene (isopropylbenzene) by introducing into two pressure reactors connected in series, 85.3 grams respectively, of catalyst comprising a 90 percent acidic, crystalline aluminosilicate zeolite containing less than 0.7 weight percent of $Na_2O$, admixed with 10 percent peptized alumina, wherein said zeolite has a unit cell size from about 24.00 Å to about 24.64 Å. The catalyst has a cloverleaf, cross-section configuration and is admixed with 1.87 volume parts (first reactor) and 1.87 volume parts (second reactor) of 6 to 8 mesh, catalytically inert quartz granules per volume of catalyst. The mixture of catalyst and quartz granules are charged to the lower 48.75 inch portion of the two reactors with a preheat section consisting of quartz granules filling 24.4 inches above the catalyst-quartz mixture in each reactor. It should be noted that the upper quartz sections of the alkylation reactors serve as feed distribution and preheat areas.

The two alkylation reactors are downflow-tubular reactors having a length of 123 inches, an inside diameter of 0.96 inches, and, in addition, each is equipped with a 0.25 inch outside diameter, central-longitudinal thermowell. The reactors are immersed in molten salt baths provided with temperature control and agitation means.

Benzene and propylene are introduced into the first alkylation reactor through a side-arm tube located above the top of the preheat section and just above the salt bath. The effluent from the first reactor, additional benzene, and propylene are introduced into the second reactor in accordance with the method used to introduce the feed stream to the first reactor. The reaction conditions are summarized in Table 4 below:

TABLE 4

|  | 1st Alkylation Reactor | 2nd Alkylation Reactor |
|---|---|---|
| Benzene/Propylene Mole Ratio | 15.0 | 16.5 |
| Pressure, p.s.i.g. | 600 | 600 |
| Temperature, °F. | 325 | 325 |
| Propylene rate ratio | 1.0 | 0.91 |
| WHSV | 10.5 | 10.8 |
| Propylene Selectivity (Based on Propyl Groups) |  |  |

TABLE 4-continued

|  | 1st Alkylation Reactor | 2nd Alkylation Reactor |
|---|---|---|
| Isopropylbenzene (Cumene) |  | 92.64 |
| Di-isopropylbenzene |  | 4.96 |
| Tri-isopropylbenzene |  | 0.40 |
| Unknowns |  | 2.00 |

A series of three continuous, water-cooled distillation columns are used to separate the combined reactor effluents from the alkylation reactors. A portion of the overhead from the first distillation column is returned to the alkylation reactors (83.06 weight percent) as recycle benzene. The remaining portion of overhead benzene (16.94 weight percent) is transported to the transalkylation reactor as recycle benzene.

The overhead from the second distillation column is cumene product, and the overhead from the third distillation column is mostly poly-alkylaromatic compounds and is recycled to a transalkylation reactor together with the remainder or benzene from the first distillation column. Heavy rejects from the third distillation column resid are discarded.

Examples of poly-alkylaromatic hydrocarbons include di-isopropylbenzenes, tri-isopropylbenzenes and unknowns. Benzene and poly-alkylaromatic hydrocarbons substantially as described above are introduced into a transalkylation reactor similar to the first alkylation reactor with the following exceptions: the reactor salt bath is replaced with a silicone bath in order to obtain a lower temperature operation and 85.3 grams of the catalyst and 127.8 grams of 6 to 8 mesh inert quartz granules are mixed in a volume distribution ratio of 0.48:1. The catalyst used in the transalkylation reactor is the same as the catalyst used in the alkylation reactor. The reaction conditions are summarized in Table 5 below:

TABLE 5

| Benzene/alkyl or Poly-alkylaromatic mole ratio | 30:1 |
|---|---|
| Pressure, p.s.i.g. | 600 |
| Temperature, °F. | 287 |
| WHSV | 2.3 |

The alkylation and transalkylation reactions give the following yield as a weight percent of feed.

TABLE 6

| Product | Yield, Wt. % of Reactor Charge |
|---|---|
| Cumene | 99.3 |
| Light Ends | 0.25 |
| Resids (Heavies) | 0.45 |

Analysis of the reaction products in the alkylation and transalkylation reactions is conducted using a Model 3920B Perkin-Elmer gas chromatograph equipped with a flame ionization detector and a 50-foot stainless steel column having an inside diameter of 0.02 inch. The column is a SCOT OS-138, which is packed with a mixture of diatomaceous earth and polyphenyl ether. The above column is marketed commercially by the Perkin-Elmer Corporation. After liquid sample induction, the gas chromatograph is held at 60° C. for 2 minutes and thereafter programmed to increase 8° C. per minute to 190° C.

EXAMPLE III

Cumene is produced from benzene and propylene in accordance with the procedure of Example II with the following exception: the catalyst in the two alkylation reactors contain 1.12 weight percent lithium. The alkylation and transalkylation reactions yield 99.52 molar percent of cumene.

EXAMPLE IV

Benzene is alkylated with propylene to produce cumene by following the procedure of Example II with the following exception: the catalyst in the two alkylation reactors contain 4.3 weight percent barium. The alkylation and transalkylation reactions yield 97.18 percent of cumene.

EXAMPLE V

Benzene is alkylated with propylene to produce cumene by following the procedure of Example II with the following exception: the catalyst in the transalkylation reactor contains 0.74 weight percent calcium. Substantially the same results are obtained using the above catalyst in the transalkylation reaction.

EXAMPLE VI

Secondary butyl benzene is produced from benzene and either n-butenes or a mixture of butene-1, trans-butene-2 and cis-butene-2 by following the procedure of Example I with the following exceptions: n-butenes or a mixture of butene-1, trans-butene-2, and cis-butene-2 are substituted for the ethylene in the alkylation reaction, and n-butylbenzene, sec-butylbenzene, tert-butylbenzene, di-sec-butylbenzenes, di-tert-butylbenzenes, and unknowns produced in the alkylation reaction are substituted for the alkyl or poly-alkylaromatic compounds in the transalkylation reactor. Analysis indicated that 92 percent of second butylbenzene is produced utilizing the alkylation and transalkylation reactions herein.

Obviously, many modifications and variations of the invention, as hereinbefore set forth, may be made without departing from the spirit and scope thereof, and therefore only such limitations should be imposed as are indicated in the appended claims.

We claim:

1. A process for the production of alkylated aromatic hydrocarbons which comprises:
   (A) contacting at least a mole-excess of an aromatic hydrocarbon and a $C_2$ to $C_4$ olefin under reaction conditions including the presence of a liquid phase in an alkylation reaction zone with an alkylation catalyst comprising a composite of a steam-stabilized hydrogen Y aluminosilicate zeolite and a mineral oxide binder, said steam-stabilized hydrogen Y aluminosilicate zeolite containing less than 0.7 weight percent of $Na_2O$ and having a unit cell size from 24.00 Å to about 24.64 Å;
   (B) separating the product from step (A) into fractions comprising (1) an aromatic hydrocarbon fraction, (2) a substantially pure mono-alkylaromatic fraction, and (3) a poly alkylaromatic hydrocarbon fraction;
   (C) recovering the mono-alkylaromatic fraction;
   (D) recycling a portion of the aromatic hydrocarbon in step (B) to the alkylation reaction zone; and
   (E) subjecting a portion of the aromatic hydrocarbon fraction and the polyalkylaromatic hydrocarbon fraction to transalkylation in a transalkylation zone under reaction conditions including the presence of a liquid phase in contact with a transalkylation catalyst comprising the composite defined in step (A), wherein the transalkylation catalyst comprises a smaller amount by weight than the alkylation catalyst.

2. The process defined in claim 1 wherein the aromatic hydrocarbon and olefin in step (A) are contacted at a molar ratio of from about 4:1 to about 25:1.

3. The process defined in claim 1 wherein the aromatic hydrocarbon in step (A) is a member selected from the group consisting of benzene, toluene and xylene and mixtures thereof.

4. The process defined in claim 1 wherein the aromatic hydrocarbon in step (A) is benzene.

5. The process defined in claim 1 wherein the olefin in step (A) is a member selected from the group consisting of ethylene, propylene, butene-1, trans-butene-2, and cis-butene-2 and mixtures thereof.

6. The process defined in claim 1 wherein the olefin in step (A) is a member selected from the group consisting of ethylene, propylene and butene-1 and mixtures thereof.

7. The process defined in claim 1 wherein the olefin in step (A) is propylene.

8. The process defined in claim 1 wherein the reaction conditions comprise a temperature of from about 250° F. to about 550° F.; a pressure of from about 50 p.s.i.g. to about 2,000 p.s.i.g.; and a weight hourly space velocity of from 1 to about 50 pounds of aromatic hydrocarbon and olefin per pound of catalyst per hour.

9. The process defined in claim 8 including a weight hourly space velocity of from 1 to about 50 pounds of aromatic hydrocarbon and poly-alkylaromatic hydrocarbon per pound of catalyst per hour.

10. The process defined in claim 1 wherein the alkylation catalyst in step (A) and transalkylation catalyst in step (E) comprise a composite of a steam stabilized hydrogen Y aluminosilicate zeolite and a mineral oxide binder in a molar ratio of from about 50:50 to about 95:5.

11. The process defined in claim 10 wherein the mineral oxide binder is a member selected from the group consisting of alumina, silica, magnesia, beryllia, zirconia, titania, thoria, chromia and clays and mixtures thereof.

12. The process defined in claim 10 wherein the mineral oxide binder is alumina.

13. The process defined in claim 1 wherein the alkylation catalyst in step (A) and transalkylation catalyst in step (E) comprise a composite having a surface area ranging from about 500 M$^2$/g to about 800 M$^2$/g; a pore volume of from about 0.5 cc/g to about 0.8 cc/g; and a compacted bulk density of from about 0.45 to about 0.75.

14. The process defined in claim 1 wherein the alkylation catalyst in step (A) and transalkylation catalyst in step (E) contain a Group IA metal selected from the group consisting of lithium, potassium, rubidium and cesium and mixtures thereof.

15. The process defined in claim 14 wherein the alkylation and transalkylation catalysts contain lithium.

16. The process defined in claim 14 wherein the alkylation and transalkylation catalysts contain from about 0.1 to about 10.0 percent by weight of a Group IA metal.

17. The process defined in claim 1 wherein the alkylation catalyst in step (A) and transalkylation catalyst in step (E) contain a Group IIA metal selected from the group consisting of beryllium, magnesium, calcium, strontium and barium and mixtures thereof.

18. The process defined in claim 17 wherein the alkylation and transalkylation catalysts contain calcium and barium.

19. The process defined in claim 17 wherein the alkylation and transalkylation catalysts contain from about 0.1 to about 10.0 percent by weight of a Group IIA metal.

20. The process defined in claim 1 wherein the aromatic hydrocarbon in fraction (1) and polyalkyl aromatic in fraction (3) of step (E) are contacted at a molar ratio of from about 1:1 to about 50:1.

21. A process for producing isopropylbenzene which comprises:
(A) contacting at least a mole-excess of benzene with propylene under reaction conditions including the presence of a liquid phase in an alkylation reaction zone with an alkylation catalyst comprising a composite of a steam-stabilized hydrogen Y aluminosilicate zeolite and a mineral oxide binder, said steam-stabilized hydrogen Y aluminosilicate zeolite containing less than 0.7 weight percent of Na$_2$O and having a unit cell size from 24.00 Å to about 24.64 Å;
(B) separating the product from step (A) into fractions comprising (1) a benzene fraction, (2) a substantially pure isopropylbenzene fraction, and (3) a poly-isopropylbenzene fraction;
(C) recovering the isopropylbenzene fraction;
(D) recycling a portion of the benzene in step (B) to the alkylation zone; and
(E) recycling a portion of the benzene and polyisopropylbenzene to transalkylation in a transalkylation zone under reaction conditions including the presence of a liquid phase in contact with a transalkylation catalyst comprising the composite defined in step (A), wherein the transalkylation catalyst comprises from about 25 to about 90 weight percent less than the alkylation catalyst.

22. The process defined in claim 21 wherein the benzene and propylene are contacted at a molar ratio of from about 4:1 to about 25:1.

23. The process defined in claim 21 wherein the reaction conditions comprise a temperature of from about 250° F. to about 550° F.; a pressure of from about 50 p.s.i.g. to about 2,000 p.s.i.g.; and a weight hourly space velocity of from about 1 to about 50 pounds of benzene and propylene per pound of catalyst per hour.

24. The process defined in claim 23 including a weight hourly space velocity of from about 1 to about 50 pounds of benzene and poly-isopropylbenzene per pound of catalyst per hour.

25. The process defined in claim 21 wherein the mineral oxide binder is a member selected from the group consisting of alumina, silica, magnesia, beryllia, zirconia, titania, thoria, chromia and clays and mixtures thereof.

26. The process defined in claim 21 wherein the mineral oxide binder is alumina.

27. The process defined in claim 21 wherein the alkylation catalyst in step (A) and transalkylation catalyst in step (E) comprise a composite having a surface area ranging from about 500 M$^2$/g to about 800 M$^2$/g; a pore volume of from about 0.5 cc/g to about 0.8 cc/g; and a compacted bulk density of from about 0.45 to about 0.75.

28. The process defined in claim 21 wherein the alkylation catalyst in step (A) and transalkylation catalyst in step (E) contain a Group IA metal selected from the froup consisting of lithium, potassium, rubidium and cesium and mixtures thereof.

29. The process defined in claim 28 wherein the alkylation and transalkylation catalysts contain lithium.

30. The process defined in claim 28 wherein the alkylation and transalkylation catalysts contain from about 0.1 to about 10.0 percent by weight of a Group IA metal.

31. The process defined in claim 21 wherein the alkylation catalyst in step (A) and transalkylation catalyst in step (E) contain a Group IIA metal selected from the group consisting of beryllium, magnesium, calcium, strontium and barium and mixtures thereof.

32. The process defined in claim 31 wherein the alkylation and transalkylation catalysts contain calcium and barium.

33. The process defined in claim 31 wherein the alkylation and transalkylation catalysts contain from about 0.1 to about 10.0 percent by weight of a Group IIA metal.

34. The process defined in claim 31 wherein the aromatic hydrocarbon and polyalkyl aromatic in step (E) are contacted at a molar ratio of from about 1:1 to about 50:1.

35. A process for producing ethylbenzene which comprises:
(A) contacting at least a mole-excess of benzene and ethylene at a molar ratio of from about 4:1 to about 25:1, in an alkylation zone with an alkylation catalyst comprising a composite of a steam-stabilized hydrogen Y aluminosilicate zeolite admixed with an aluminum oxide binder in a molar ratio of from about 70:30 to about 90:10, under reaction conditions comprising a temperature of from about 300° F. to about 500° F., at a pressure of from about 150 p.s.i.g. to about 700 p.s.i.g., a weight hourly space velocity of from about 1 to about 50 pounds of benzene and ethylene per pound of catalyst per hour, said reaction conditions including the presence of a liquid phase and said steam-stabilized hydrogen Y aluminosilicate zeolite containing less than 0.7 weight percent of $Na_2O$ and having a unit cell size from about 20.00 Å to about 24.64 Å;
(B) separating the product from step (A) into fractions comprising (1) a benzene fraction, (2) a substantially pure ethylbenzene fraction, and (3) a poly-ethylbenzene fraction;
(C) recovering the ethylbenzene fraction;
(D) recycling a portion of the benzene in step (B) to the alkylation zone, and
(E) subjecting a portion of benzene and the polyethylbenzene to transalkylation in a transalkylation zone under reaction conditions including the presence of a liquid phase in contact with a transalkylation catalyst comprising the composite defined in step (A); wherein the transalkylation catalyst comprises from about 25 to about 90 weight percent less than the alkylation catalyst.

36. A process for producing isopropylbenzene which comprises:
(A) contacting at least a mole-excess of benzene and propylene at a molar ratio of from about 4:1 to about 25:1, in an alkylation zone with an alkylation catalyst comprising a composite of a steam-stabilized hydrogen Y aluminosilicate zeolite admixed with an aluminum oxide binder in a molar ratio of from about 70:30 to about 90:10, under reaction conditions comprising a temperature of from about 300° F. to about 500° F., at a pressure of from about 150 p.s.i.g. to about 700 p.s.i.g., a weight hourly space velocity of from about 1 to about 50 pounds of benzene and ethylene per pound of catalyst per hour, said reaction conditions including the presence of a liquid phase, and said steam-stabilized hydrogen Y aluminosilicate zeolite containing less than 0.7 weight percent of $Na_2O$ and having a unit cell size from about 24.00 Å to about 24.64 Å;
(B) separating the product from step (A) into fractions comprising (1) a benzene fraction, (2) a substantially pure isopropylbenzene fraction, and (3) a poly isopropylbenzene fraction;
(C) recovering the isopropylbenzene fraction;
(D) recycling a portion of the benzene in step (B) to the alkylation zone; and
(E) subjecting a portion of benzene and the poly isopropylbenzene to transalkylation in a transalkylation zone under reaction conditions, including the presence of a liquid phase, in contact with a transalkylation catalyst comprising the composite defined in step (A), wherein the transalkylation catalyst comprises from about 25 to about 90 weight percent less than the alkylation catalyst.

37. A process for the production of alkylated aromatic hydrocarbons which comprises:
(A) contacting at least a mole-excess of an aromatic hydrocarbon and a $C_2$ to $C_4$ olefin under reaction conditions, including the presence of a liquid phase, in an alkylation reaction zone with an alkylation catalyst comprising a composite of a steam-stabilized hydrogen Y aluminosilicate zeolite and a mineral oxide binder, said steam-stabilized hydrogen Y aluminosilicate zeolite containing less than 0.7 weight percent of $Na_2O$, having a unit cell size from 24.00 Å to about 24.64 Å, and containing a Group IA metal or a Group IIA metal of the Periodic Table;
(B) separating the product from step (A) into fractions comprising (1) an aromatic hydrocarbon fraction, (2) a substantially pure mono-alkylaromatic fraction, and (3) a poly alkylaromatic hydrocarbon fraction;
(C) recovering the alkylaromatic fraction;
(D) recycling a portion of the aromatic hydrocarbon in step (B) to the alkylation reaction zone; and
(E) subjecting a portion of the aromatic hydrocarbon and the polyalkylaromatic hydrocarbon to transalkylation in a transalkylation zone under reaction conditions, including the presence of a liquid phase, in contact with a transalkylation catalyst comprising the composite defined in step (A), wherein the transalkylation catalyst comprises from about 25 to about 90 weight percent less than the alkylation catalyst.

38. The process defined in claim 37 wherein the alkylation catalyst in step (A) and transalkylation catalyst in step (E) contain a Group IA metal selected from the group consisting of lithium, potassium, rubidium and cesium and mixtures thereof.

39. The process defined in claim 37 wherein the alkylation catalyst in step (A) and transalkylation catalyst in step (E) contain a Group IIA metal selected from the group consisting of beryllium, magnesium, calcium, strontium and barium and mixtures thereof.

* * * * *